US009980661B2

United States Patent
Saba et al.

(10) Patent No.: US 9,980,661 B2
(45) Date of Patent: May 29, 2018

(54) ELECTROCARDIOGRAM RECONSTRUCTION FROM IMPLANTED DEVICE ELECTROGRAMS

(75) Inventors: Samir F. Saba, Pittsburgh, PA (US); Jeffrey L. Williams, Lebanon, PA (US); George S. Mendenhall, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 1334 days.

(21) Appl. No.: 13/479,562

(22) Filed: May 24, 2012

(65) Prior Publication Data

US 2013/0317376 A1 Nov. 28, 2013
US 2017/0367605 A9 Dec. 28, 2017

Related U.S. Application Data

(62) Division of application No. 12/233,297, filed on Sep. 18, 2008, now Pat. No. 8,200,318.

(60) Provisional application No. 60/994,682, filed on Sep. 21, 2007.

(51) Int. Cl.
*A61B 5/04* (2006.01)
*A61B 5/0452* (2006.01)
*A61B 5/0464* (2006.01)
*A61B 5/00* (2006.01)

(52) U.S. Cl.
CPC .......... *A61B 5/0452* (2013.01); *A61B 5/0464* (2013.01); *A61B 5/686* (2013.01)

(58) Field of Classification Search
CPC ...... A61B 5/0452; A61B 5/0464; A61B 5/686

USPC .......................................... 600/509
See application file for complete search history.

(56) References Cited

U.S. PATENT DOCUMENTS

| | | | |
|---|---|---|---|
| 3,868,567 A | 2/1975 | Ekstrom | 324/77 |
| 4,546,776 A | 10/1985 | Bellin et al. | 128/704 |
| 4,649,924 A | 3/1987 | Taccardi | 128/642 |
| 4,679,144 A | 7/1987 | Cox et al. | 364/417 |
| 5,003,983 A | 4/1991 | Dingwall et al. | 128/704 |
| 5,143,089 A | 9/1992 | Alt | 128/784 |
| 5,738,104 A | 4/1998 | Lo et al. | 128/706 |
| 6,187,032 B1 | 2/2001 | Ohyu et al. | 600/409 |
| 6,324,421 B1 | 11/2001 | Stadler et al. | 600/509 |
| 6,397,100 B2 | 5/2002 | Stadler et al. | 600/509 |

(Continued)

FOREIGN PATENT DOCUMENTS

WO WO 2006124960 A2 * 11/2006 ........... A61B 5/0002

OTHER PUBLICATIONS

Barold et al., "Prospective evaluation of new and old criteria to discriminate between supraventricular and ventricular tachycardia in implantable defibrillators," *Pacing Clin Electrophysiol*, 21: 1347-1355 (1998).

(Continued)

*Primary Examiner* — Amanda Patton
(74) *Attorney, Agent, or Firm* — Medlen & Carroll, LLP

(57) ABSTRACT

A method of reconstruction of the standard 12-lead surface EKG given values of the electrical potential from an implanted medical device is described. This implanted device can be oriented in an arbitrary fashion and reconstruction technique is obtained through physical measurement of the orientation of the implanted device or correlation with a standard 12-lead EKG obtained from the patient.

14 Claims, 7 Drawing Sheets

(56) References Cited

U.S. PATENT DOCUMENTS

| | | | |
|---|---|---|---|
| 6,466,640 B1* | 10/2002 | Taguchi | A61B 6/032 378/15 |
| 6,766,190 B2* | 7/2004 | Ferek-Petric | A61B 5/0464 600/509 |
| 6,813,514 B1 | 11/2004 | Kroll et al. | 600/509 |
| 6,980,850 B1 | 12/2005 | Kroll et al. | 600/509 |
| 7,447,544 B1 | 11/2008 | Kroll | 607/9 |
| 7,620,449 B2 | 11/2009 | Shvilkin et al. | 600/517 |
| 2006/0149156 A1 | 7/2006 | Cochran et al. | 600/509 |
| 2007/0197957 A1* | 8/2007 | Hunter | A61L 31/10 604/65 |
| 2007/0244403 A1 | 10/2007 | Natarajan et al. | 600/509 |
| 2009/0187097 A1* | 7/2009 | Saba | A61B 5/04012 600/424 |

OTHER PUBLICATIONS

Buxton et al., "Current approaches to evaluation and management of patients with ventricular arrhythmias," *Med Health RI*, 84(2): 58-62 (2002).

Gold et al., "A new defibrillator discrimation algorithm utilizing electrogram morphology analysis," *Pacing Clin Electrophysiol*, 22: 179-182 (1999).

Lampert et al., "Management of arrhthmias," *Clin Geriatr Med*, 16(3): 593-618 (2000).

Schaumann et al., "Enhanced detection criteria in implantable cardioverter-defibrillator to avoid inappropriate therapy," *Am J Cardiol*, 78: 42-50 (1996).

Tanaka, "An overview of fifth-generation implantable cardioverter defibrillator," *Ann Thorac Cardiovasc Surg*, 4: 303-311 (1998).

Britannia Academic Edition defining electrocardiographt, http://www.britannica.com/EBchecked/topic/182988/electrocardiography.

* cited by examiner

Reconstructed Lead I (rEKG)

Surface Measured Lead I (sEKG)

Reconstructed Lead III (rEKG)

Surface Measured Lead III (sEKG)

Reconstructed Lead V1

Surface Measured Lead V1

ELECTROCARDIOGRAM RECONSTRUCTION FROM IMPLANTED DEVICE ELECTROGRAMS

This is a divisional application that claims priority to U.S. patent application Ser. No. 12/233,297 (now issued as U.S. Pat. No. 8,200,318), filed on Sep. 18, 2008, which claims priority to U.S. provisional patent application Ser. No. 60/994,682, filed Sep. 21, 2007, each of which is herein incorporated by reference in its entirety.

FIELD OF INVENTION

The present invention is related to the field of cardiology. In one embodiment, the present invention contemplates generating a reconstructed electrocardiogram (rEKG) free of extraneous electrical activity. For example, an implanted device detects intracardiac electromyograms (EMG's) that are compared with a traditional surface EKG pattern (i.e., for example, a 12-lead surface EKG; sEKG) to calculate EMG/sEKG correlation parameters. The EMG/sEKG correlation parameters are then used to transform the EMG vectors into an rEKG. Such rEKGs are useful for diagnostic and therapeutic purposes. The implanted device may be a sensor device, a pacemaker and/or a defibrillator.

BACKGROUND OF THE INVENTION

Implanted devices are well suited for recording intracardiac electrical potentials (i.e., for example, electromyograms; EMG) because they are isolated from electrical signals from outside the body. The morphology of an EMG reflects local and global electrical activity of the heart. There has been a dramatic increase in the utilization of implantable cardioverter defibrillators (ICD's) and pacemakers and as a result, there is an abundance of EMG information available. However, few attempts have been made to extract information from the EMG's aside from the discrimination of supraventricular (SVT) and ventricular tachycardias (VT). One reason that these attempts have not been successful is due to the fact that the unknown and arbitrary orientation of the recording device prevents rapid interpretation by medical personnel.

What is needed is an electrocardiogram reconstruction technique using electrical potentials obtained from a device implanted within a patient.

SUMMARY

The present invention is related to the field of cardiology. In one embodiment, the present invention contemplates generating a reconstructed electrocardiogram (rEKG) free of extraneous electrical activity. For example, an implanted device detects intracardiac EMG's that are compared with a traditional surface EKG pattern (i.e., for example, a 12-lead surface EKG; sEKG) to calculate EMG/sEKG correlation parameters. The EMG/sEKG correlation parameters are then used to transform the EMG vectors into an rEKG. Such rEKGs are useful for diagnostic and therapeutic purposes. The implanted device may be a sensor device, a pacemaker and/or a defibrillator.

In one embodiment, the present invention contemplates a method, comprising: a) providing: i) a traditional electrocardiogram (sEKG) derived from skin surface electrodes; ii) at least one intracardiac electromyogram (EMG) derived from an implanted cardiac device, wherein said device is connected a plurality of electrode leads; b) comparing said sEKG and said EMG to obtain an EMG/sEKG correlation parameter; and c) calculating a reconstructed electrocardiogram using said correlation parameter and said EMG. In one embodiment, the electrode leads are selected from the group comprising right-sided leads or left-sided leads. In one embodiment, the leads are selected from the group comprising extended V-leads or extended A-leads. In one embodiment, the sEKG is collected at the same time as said EMG. In one embodiment, the sEKG is collected at a different time as said EMG. In one embodiment, the skin surface electrodes are in known positions. In one embodiment, the device electrode leads are in known positions. In one embodiment, the known positions are determined by a technique selected from the group consisting of radiography, ultrasonography, computerized acoustic tomography, and magnetic imaging resonance, or other imaging techniques, including but not limited to, impedance localization, or magnetic mapping techniques In one embodiment, the present invention contemplates a system, comprising: a) an implanted cardiac device comprising a positional sensor, wherein said device is connected to a plurality of electrode leads, and wherein said leads provide intracardiac electromyograms (EMG); b) a computer comprising at least one microprocessor, wherein said computer is operably linked to said cardiac device; c) a plurality of EMG/sEKG correlation parameters residing on said at least one microprocessor, wherein each parameter is derived from differential data, from said positional sensor; and d) an algorithm residing on said at least one microprocessor, wherein said algorithm calculates a reconstructed EKG (rEKG) using said EMG and said correlation parameters or is calculated through an orthogonal vectorcardiogram (VCG) as an intermediate. In one embodiment, the rEKG is calculated on-demand. In one embodiment, the rEKG is calculated automatically and continuously. In one embodiment, the automatic calculation is performed in response to alterations in said EMG. In one embodiment, the automatic calculation is performed in response to alterations in said positional sensor data. In one embodiment, the at least one microprocessor further comprises a plurality of rEKG threshold exceedances. In one embodiment, the rEKG threshold exceedance provides a warning signal. In one embodiment, the rEKG threshold exceedance provides a preliminary diagnosis. In one embodiment, the method further comprises a transmission device capable of sending data selected from the group consisting of EMG, EMG/sEKG correlation parameters, positional data, and rEKG to a remote location.

A method, comprising: a) providing: i) a subject exhibiting symptoms of a cardiac disease; ii) a system capable of calculating a reconstructed electrocardiogram (rEKG) specific for said subject; iii) a testing parameter known to detect said cardiac disease; b) administering said testing parameter to said subject under conditions such that said rEKG detects said cardiac disease. In one embodiment, the detected cardiac disease comprises ischemia. In one embodiment, the method detects cardiac structural diseases, including but not limited to, cardiac muscle diseases (i.e., for example, pericarditis, myocarditis, etc.). In one embodiment, the method detects pulmonary diseases (i.e., for example, pulmonary embolism, pulmonary hypertension, chronic obstructive pulmonary disease, etc.). In one embodiment, the method detects central nervous system disorders (i.e., for example, stroke, cranial bleeding, etc.). In one embodiment, the method detects cardiac conduction system diseases (i.e., for example, sick sinus syndrome, atrioventricular nodal block of degrees 1, 2 and 3, etc.) In one embodiment, the detected cardiac disease comprises electrolyte abnormalities. In one embodiment, the detected cardiac disease comprises a myocardial infarction. In one embodiment, the detected cardiac disease comprises heart rhythm discrimination. In one embodiment, the testing parameter comprises at least one medication. In one embodiment, the testing parameter comprises a stress test. In one embodiment, the testing parameter comprises a salt complex.

Definitions

The term "traditional electrocardiogram" or "standard electrocardiogram" as used herein is abbreviated as "sEKG" and refers to a heart rhythm tracing generated by collecting electrical signals from skin surface electrodes. These sEKGs comprise the P-Q-R-S-T heart waveform complex useful in diagnosing a variety of cardiac diseases.

The term "skin surface electrodes" as used herein refers to any electrically conductive material placed upon the skin surface capable of transmitting electrical potential information. A properly placed array of skin surface electrodes connected to a conventional electrocardiograph device can result in the production of an sEKG.

The term "intracardiac electromyogram" as used herein is abbreviated as "EMG" and refers to a cardiac muscle contractility tracing generated by collecting electrical signals from electrode leads placed in specific heart locations. These EMGs comprise relative contraction/relaxation rates for each heart location useful in diagnosing a variety of cardiac disorders.

The term "electrode leads" as used herein refer to any electrically conductive material placed on the exterior or interior surface of a heart muscle (i.e., for example, ventricular muscle and/or atrial muscle) capable of transmitting electrical potential information. A properly placed array of electrode leads connected to an implanted cardiac device (i.e., for example, a defibrillator and/or a pacemaker) can result in the production of an EMG.

The term "EMG/sEKG correlation parameter" as used herein refers to a product of an algorithm comprising EMG and sEKG data calculations. This algorithm may vary depending upon the relative positioning of the heart within the chest cavity of the same subject (i.e., for example, an EMG/sEKG correlation parameter taken in the supine position will differ from an EMG/sEKG correlation parameter taken in the standing position). Consequently, the correlation parameter may be used to correct for an unknown electrode lead position in order to provide an rEKG.

The term "reconstructed electrocardiogram" as used herein is abbreviated as "rEKG" and refers to the generation of a conventional P-Q-R-S-T heart waveform pattern by utilizing an algorithm based upon an EMG/sEKG correlation parameter and EMG data.

The term "implanted cardiac device" as used herein refers to any device capable of providing functional heart data. For example, such a device may comprise a pacemaker, a defibrillator or other sensor device. Further, these devices may also comprise a positional sensor that is calibrated to detect gravitational forces such that the anatomical positioning of the heart may be determined. Such devices may be hardwired, or preferably are wireless, to support data communication with remote data collection devices (i.e., for example, a desktop computer and/or laptop computer). An implanted cardiac device is operably connected to a plurality of electrode leads capable of two-way electrical signal transmission. For example, electrode leads may include, but are not limited to, right-sided leads (contacting the right side of the heart), left-sided leads (contacting the left side of the heart), extended V-leads (contacting the ventricle) and/or extended A-leads (contacting the atria).

As used herein, the term "atria" refers to the upper principal cavity of the heart auricle (i.e., the sinus venosus) and is situated posteriorly to the smaller cavity of the auricle, the appendix auricula. The human heart comprises two atria, one on the left side of the heart and a second on the right side of the heart. Consequently, the term "atrial" references any matter of, or concerning, either one or both atria.

As used herein, the term "ventricle" refers to the lower, and largest, compartment of the heart. The human heart comprises two ventricles, one on the left side of the heart and a second on the right side of the heart. Consequently, the term "ventricular" references any matter of, or concerning, either one or both ventricles.

The term "at the same time" as used herein refers to the collection of different data sets in near real-time. While not necessarily simultaneously, it is preferred that such data sets are collected within 5-100 msec, preferably within 25-75 msec, and most preferably within 30-50 msec of each other.

The term "at different times" as used herein refers to the collection of different data sets separated in time. For example, such time separations may include, but are not limited to, minutes, hours, days and/or years.

The term "computer" as used herein refers to any device capable of performing serial and/or parallel mathematical calculations utilizing an algorithm (i.e., for example, a software program) that resides within the device. Generally, such algorithms reside on a plurality of microprocessors that are in electrical communication with the computer, wherein the microprocessors can receive, store, and transmit data.

As used herein, the term "microprocessor" refers to a programmable digital electronic component that incorporates the functions of a central processing unit on a single semi-conducting integrated circuit.

As used herein, the term "storage memory" refers to any electronic means that is capable of retaining digitized information or computer software programs. The digitized information may be binary or complex formulas or equations capable of receiving, and processing, input from atrial or ventricular sensing leads.

The term "differential data" as used herein refers to the comparison of two or more data sets describing the same endpoint but under dissimilar environmental conditions. For example, the calculation of an EMG/sEKG correlation parameter when a subject is supine, represents differential data when compared to the calculation of an EMG/sEKG correlation parameter with the same subject is standing.

The term "on-demand" as used herein refers to an instruction to perform an rEKG calculation a single time. Such an instruction is generally provided by a medical technician, doctor, and/or patient in response to an unexpected medical condition, or as part of an expected testing protocol.

The term "automatically" as used herein refers to an instruction to perform an rEKG calculation whenever specific, pre-identified, conditions exist. Such conditions may be part of an algorithm residing on a computer microprocessor that trigger the calculation of an rEKG. The series of rEKGs are then placed in memory storage for later retrieval.

The term "threshold exceedances" as used herein refers to any preset limit for a physiological condition reflected by an rEKG value. Generally, when such preset limits are exceeded a subject's medical condition has been significantly altered that may, or may not, require medical attention. For example, a threshold exceedance may signal a warning that medication administration is overdue. Alternatively, a threshold exceedance may provide sufficient information such that medical personnel can establish a preliminary diagnosis for a suspected cardiac disease.

The term "symptom" as used herein refers to any alteration of a measurable biological response (i.e., for example, respiration, heart rate, blood cell count, hormone levels etc.) that are outside normal limits as generally accepted by the medical profession.

The term "cardiac disease" as used herein refers to any alteration of heart function based upon parameters including, but not limited to, electrical and/or muscular balance. Specific cardiac diseases may include, but are not limited to, myocardial infarction, ischemic cardiomyopathy, angina pectoris, heart rhythm arrhythmias, tachycardias, congestive heart failure, and/or atrial fibrillation, nerve conduction disorders, thrombophilia, atherosclerosis, hypertension, arteriosclerosis, cardiomyopathy, hypertension, and/or arterial or venous stenosis, or valvular heart disease "Symptoms of cardiac disease" as used herein refers to any clinical manifestation of a disease state associated with the heart and the central or peripheral arterial and venous vasculature. For example, said clinical manifestations include, but are not limited to pain, weakness, high blood pressure, elevated plasma cholesterol, elevated plasma fatty acids, tachycardia, bradycardia, abnormal electrocardiogram, external or internal bleeding, headache, dizziness, nausea and vomiting. Thus, a patient suffering from, or exhibiting symptoms of, cardiovascular disease may detect certain symptoms (i.e., pain), while other symptoms may not be noticeable to the patient, but are detectable by a health care provider (i.e., elevated blood pressure).

As used herein, the term "patient" or "subject" refers to a human or non-human organism that is either symptomatic or asymptomatic for cardiovascular disease. Preferably, a human patient is under the supervision of a physician or hospitalized.

As used herein the phrase, "patients at risk for cardiac disease" refer to patients who have an increased probability, as compared to the general population, of developing some form of cardiac disease in their lifetime. Patients at risk for cardiac disease generally have one or more risk factors for cardiac disease. Risk factors for cardiac disease include, but are not limited to, a history of smoking, a sedentary lifestyle, a family history of cardiovascular disease, lipid metabolic disorders, diabetes mellitus and obesity.

The term "testing parameter" as used herein refers to any substance or activity that modifies heart function such that an underlying cardiac disease may be detected. For example, the administration of a medication may detect angina and/or ischemia (i.e., for example, nitroglycerin). Alternatively, administering a subject to a treadmill stress test may detect a risk for myocardial infarction. Further, administering a subject a salt complex (i.e., for example, a mixture of sodium chloride and potassium chloride) may detect electrolyte imbalances.

As used herein, the term "system" refers to any integrated single device, or multiple devices connected together, that function in a coordinated manner to produce a desired result. One example illustrated herein, describes a system that calculates an rEKG in real-time with the collection of EMG data.

As used herein, the term "algorithm" refers to a precise list of precise steps, and/or a finite list of well-defined instructions, for accomplishing some task that, given an initial state, will terminate in a defined end-state.

The term "augmented vector right" or "AvR" as used herein, refers to any electrode lead having a positive electrode on the right arm. The negative electrode comprises a combination of the left arm electrode and the left leg electrode, which "augments" the signal strength of the positive electrode on the right arm. The "AvR" represents one (1) of the standard twelve (12) projections of the 12-lead EKG.

The term "augmented vector left" or "AvL" as used herein, refers to any electrode lead having a positive electrode on the left arm. The negative electrode comprises a combination of the right arm electrode and the left leg electrode, which "augments" the signal strength of the positive electrode on the left arm. The "AvL" represents one (1) of the standard twelve (12) projections of the 12-lead EKG.

The term "augmented vector foot" or "AvF" as used herein, refers to any electrode lead having a positive electrode on the left leg. The negative electrode is a combination of the right arm electrode and the left arm electrode, which "augments" the signal of the positive electrode on the left leg. The "AvF" represents one (1) of the standard twelve (12) projections of the 12-lead EKG.

DETAILED DESCRIPTION

Figure 1:
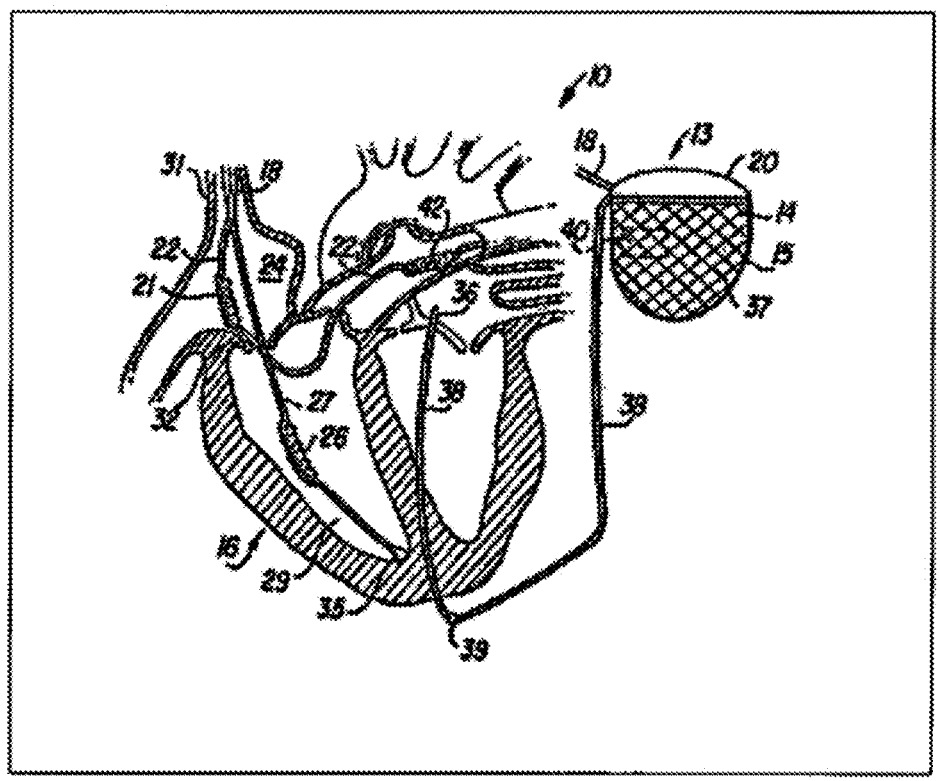
FIG. 1 depicts a cutaway drawing of an exemplary human heart showing the configuration of one embodiment of dual chamber implantable cardiac pacer/defibrillator.
Figure 2:
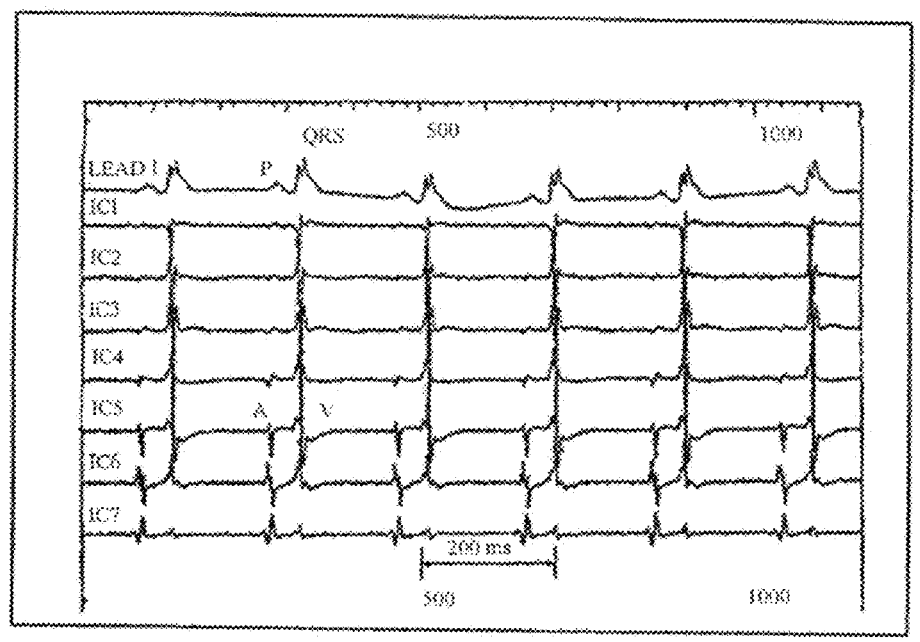
FIG. 2 shows an exemplary normal sinus rhythm tracing in a mouse.

The present invention is related to the field of cardiology. In one embodiment, the present invention contemplates generating a reconstructed electrocardiogram (rEKG) free of extraneous electrical activity. For example, an implanted device detects intracardiac electrograms (EMG's) that are compared with a traditional surface EKG pattern (i.e., for example, a 12-lead surface EKG; sEKG) to calculate EMG/sEKG correlation parameters. The EMG/sEKG correlation parameters are then used to transform the EMG vectors into an rEKG. Such rEKGs are useful for diagnostic and therapeutic purposes. The implanted device may be a sensor device, a pacemaker and/or a defibrillator.

I. Heart Function

The operation of the heart is regulated by electrical signals produced by the heart's sinoatrial (SA) node. Each signal produced by the SA node spreads across the atria and ventricles of the heart, depolarizing the muscle fibers as it spreads. Atrial and ventricular contractions occur as the signal passes. After contracting, the myocardial cells repolarize during a short period of time, returning to their resting state. Once repolarized, the muscle cells are ready to be depolarized again by a signal from the SA node.

At rest, the normal adult SA node produces a signal approximately 60 to 85 times a minute, causing the heart muscle to contract, and thereby pumping blood to the remainder of the body. This constitutes the repetitive, cyclic behavior of the heart. Each cycle in the operation of the heart is called a cardiac cycle.

Atrial geometry, atrial anisotropy, and histopathologic changes in the left or right atria can, alone or together, form anatomical obstacles. The obstacles can disrupt the normally uniform propagation of electrical impulses in the atria. These anatomical obstacles (called "conduction blocks") can cause the electrical impulse to degenerate into several circular wavelets that circulate about the obstacles. These wavelets, called "reentry circuits," disrupt the normally uniform activation of the left and right atria. Abnormal, irregular heart rhythm called arrhythmia, results. This form of arrhythmia is called atrial fibrillation, which is a very prevalent form of arrhythmia.

To analyze the heart's operation, a variety of techniques have been developed for collecting and interpreting data concerning the electrical activity of the heart. One of the most basic of these approaches is the electrocardiogram (EKG). As an electrical signal spreads across the heart, an EKG repetitively measures the voltages at various electrodes relative to a designated "ground" electrode. The EKG typically plots each lead over an interval of time such that the heart's electrical activity for one or more cardiac cycles is displayed for purposes of monitoring or analysis. The three most common EKG's are known as the "12 lead", the "18 lead," and the vector cardiograph.

A cardiac cycle as measured by the EKG is partitioned into three main elements, which reflect the electrical and mechanical operation of the heart. The portion of a cardiac cycle representing atrial depolarization is referred to as a "P-wave." Depolarization of the ventricular muscle fibers is represented by "Q", "R", and "S" points of a cardiac cycle. Collectively these "QRS" points are called an "R-wave" or a "QRS complex." The portion of a cardiac cycle representing repolarization of the ventricular muscle fibers is known as a "T-wave." It is through the use of an EKG that one is able to determine whether fibrillation is or is not occurring and allows one to manipulate the heart tissue to provide treatment.

II. Pacemakers

A pacemaker maintains the heart rate of a patient between a certain programmable range. For example, in humans that range is typically between 60 to 80 beats per minute (lower rate) and 120 to 160 beats per minute (upper rate). In one embodiment, the present invention contemplates a pacemaker for stimulating the independent conduction zones and reestablishing functional communication between the zones. A pacemaker automatically applies a pacing impulse to the heart of sufficient magnitude to depolarize the tissue. The device is adapted to continue delivering intermittent pacing to the heart in the event that the heart fails to return to its normal behavioral pattern, and has the ability of automatically regaining sensing control over a functional heart, thereby insuring that further pacing is inhibited.

The pacemaker circuit comprises two basic subsystems; a sensing system, which continuously monitors heart activity; and a stimulation system which upon receiving a signal from the sensing system applies a pacing impulse to the myocardium through an intravascular electrical lead. A first bipolar lead may be coupled to the pulse generator and has an electrode located at its distal end to sense and pace the atrium. Alternatively, the atrial leads may comprise separate sensing and pacing electrodes. A second bipolar lead coupled to the generator is used for sensing and pacing the ventricle. Alternatively, the ventricular leads may comprise separate sensing and pacing electrodes. A circuit is provided for applying impedance measuring current pulses between one of these electrodes and the others.

A. Sensing Elements of a Pacemaker

In a standard dual chambered pacemaker, the sensing circuits monitor activity both in the atrium and ventricle. If a sensed event occurs in the atrium, this initiates a ventricular paced event if no ventricular activity occurs during the programmed atrio-ventricular delay. If no sensing occurs in the atrium or ventricle, pacing is initiated to maintain the programmed lower rate.

When the pacemaker device is used for the present invention, similar sensing algorithms will be useful in the appropriate pacing of the various intracardiac segments. It is particularly desirable that the pacemaker include a sensor of a physiologic parameter related to demand for cardiac output, such as an activity sensor, a respiration sensor or an oxygen saturation sensor. Various dual chamber pacing devices have incorporated some form of sensor to provide a physiologic pacing rate. Similar sensing is contemplated for the present invention to maintain a physiologic rate.

B. Pacing Elements

In a standard dual chamber pacemaker, pacing of both atrium and ventricle is possible. In the current invention, pacing of the various elements will take place once requested by the sensing algorithm. The standard burst generator pacemaker employs appropriate technology for the generation of stimulation pulses in the form of individual pulses or pulse trains having an amplitude up to 7 V and a pulse width of up to 1 msec. Most pacemakers have these parameters as a programmable option. The pacing rate is also programmable in most pacemakers and the range is between 35 to 160 beats/min.

Given that the circuitry for pulse generation has become well known to those skilled in the art, no detailed disclosure is included herein. Specific timing, amplitude, duration and the number of pulses is controlled by a microprocessor via data bus under the control of a program stored in memory.

III. Implantable Cardiac Defibrillators

Implantable cardiac defibrillators (ICDs) have significantly reduced the risk of sudden death following hospital discharge, but arrhythmia risk and associated mortality remains an important problem. Buxton et al., *Current Approaches To Evaluation And Management Of Patients With Ventricular Arrhythmias*, Med Health R I, 84(2):58-62 (2001) Arrhythmias are known to occur in patients having congestive heart failure, atrial fibrillation, ventricular tachyarrhythmias, and bradyarrhythmias. Atrial fibrillation, in particular, is treatable with rate control anticoagulation or cardioversion followed by maintenance of sinus rhythm. In patients surviving malignant ventricular arrhythmias, however, implanted cardiac defibrillators are especially beneficial. Specifically, in patients with coronary artery disease, decreased ejection fraction, with or without nonsustained ventricular tachycardia, defibrillator implantation can improve survival. Lampert et al., *Management Of Arrhythmias*, Clin Geriatr Med, 16(3):593-618 (2000)

Identifying the mechanism of an arrhythmia based on intracardiac electrograms has become a challenge in the clinical use of implantable cardiac defibrillators. Implantable cardiac defibrillators are primarily designed to deliver therapy for life-threatening ventricular arrhythmias but frequently deliver inappropriate shocks during supraventricular tachycardias. Tanaka S., *An Overview Of Fifth-Generation Implantable Cardioverter Defibrillator*, Ann Thorac Cardiovasc Surg., 4:303-311 (1998); Thompson et al., supra; Gold et al., *A New Defibrillator Discrimination Algorithm Utilizing Electrogram Morphology Analysis*, Pacing Clin Electrophysiol. 1999; 22:179-182 (1999); Barold et al., *Prospective Evaluation Of New And Old Criteria To Discriminate Between Supraventricular And Ventricular Tachycardia In Implantable Defibrillators*, Pacing Clin Electrophysiol., 21:1347-1355 (1998); and Schaumann et al., *Enhanced Detection Criteria In Implantable Cardioverter-Defibrillator To Avoid Inappropriate Therapy*, Am J. Cardiol., 78:42-50 (1996)

In one embodiment, the present invention contemplates an implantable cardiac defibrillator 13 attached to pacemaker 14. See, FIG. 1. It is not intended that the scope of the present invention by limited by the herein exemplary device. In fact, many possible engineering designs are compatible with the embodiments described herein.

The pacemaker/defibrillator is implanted in a surgically-formed pocket in the flesh of the patient's chest 10, or other desired location of the body. Signal generator 14 is conventional and incorporates electronic components for performing signal analysis and processing, waveform generation, data storage, control and other functions, power supply 40 (battery or battery pack), which are housed in a metal case (can) 15 compatible with the tissue and fluids of the body (i.e., biocompatible). The device is microprocessor-based with substantial memory, logic and other components to provide the processing, evaluation and other functions necessary to determine, select and deliver appropriate therapy including electrical defibrillation and pulses of different energy levels and timing for ventricular defibrillation, cardioversion, and pacing to the patient's heart 16 in response to ventricular arrhythmia and supraventricular tachycardia.

Composite electrical lead 18 which includes separate leads 22 and 27 with distally located electrodes is coupled at the proximal end to signal generator 14 through an electrical connector 20 in the header of case 15. Preferably, case 15 is also employed as an electrode such as electrical ground, for unipolar sensing, pacing or defibrillation. Unlike the defibrillator devices used in previous methods, the signal generator and lead(s) of the present invention may be implemented for atrial and ventricular sensing, pacing and defibrillation. Defibrillating shocks of appropriate energy level may be applied between the case and electrode 21 on lead 22 implanted in the right atrium 24 through the superior vena cava 31, or between the case and electrode 26 on lead 27 implanted through the superior vena cava in the right ventricle 29. Leads 22 and 27 and their associated distal tip electrode 32 (to a separate conductor) and distal tip electrode 35 (also to a separate conductor within the lead), respectively, may be used for both a sensing lead and a pacing lead in conjunction with the circuitry of signal generator 14. One of skill in the art may easily recognize that separate sensing and pacing leads are also compatible with this described system. To that end, electrode 32 is positioned in the right atrium against either the lateral or anterior atrial wall thereof, and electrode 35 is positioned in the right ventricle at the apex thereof.

Active or passive fixation of the electrodes may be used to assure suitable excitation. Tip electrode tip 35 preferably has a standard 4 to 8 millimeter (mm) configuration, and is provided with soft barbs (tines) to stabilize its position in the ventricle. Each of the electrodes, those used for defibrillation and cardioversion, as well as those used for sensing and for pacing, are electrically connected to separate conductors in leads 22 and 27.

If desired, rather than simply using metal case 15 as an electrode, a conductive pouch 37 comprised of a braided multiplicity of carbon fine, individual, predominantly isotropic wires such as described in U.S. Pat. No. 5,143,089 (herein incorporated by reference) is configured to receive, partly enclose and maintain firm electrical contact with the case. This serves to enhance the effectiveness of the anodal electrode of the case and establish a better vector for the electric field produced by the defibrillation shock waveform, and thereby lower the defibrillation threshold. The conductive pouch can be electrically connected directly to an extension lead 38 composed of similar carbon braid of about 7 french diameter which is implanted subcutaneously for connection to an epicardial or pericardial patch electrode (not shown) or as a wire electrode (as shown) through an opening formed by puncture surgery at 39. The conductor for electrode 36 of lead 38 may be implanted subcutaneously to a point 39, and then by puncture surgery through the thoracic cage and the pericardial sac, under a local anesthetic. The lead 38 is run parallel to the sternum, through the puncture, and then through the patient's thoracic cage and into the pericardial sac. It may even be threaded through the thoracic cage, the pericardial space about the left ventricle and atrium, and back along the right atrial appendage, external to the heart. The distal end 36 of lead 38 is preferably placed close to the left atrium of the patient's heart to provide an increase in electric field strength and support the strong vector of the electric field according to the heart chamber to be defibrillated. Selection of the chamber (i.e., atrium or ventricle) which is to undergo defibrillation is made by choosing the appropriate endocardial counter-electrode (21 or 26, respectively) to be energized together with the carbon electrode, if the case 15 or conductive pouch 37 is not used directly as the other electrode.

Fabricating the electrode portion of conductor 38 (from the point of entry 39 into the thoracic cage) of carbon braid provides the desirable features described earlier herein. Proper intracardiac positioning improves the vector for defibrillation through the atrium as well as the ventricle.

Atrial coil electrode 21 is used for bipolar sensing as well as a counter-electrode for defibrillation. Hence, electrode 21 is preferably also composed of a braided carbon fiber material described in the '089 patent, to take advantage of its very low polarization and low defibrillation threshold, to allow the intrinsic rhythm to be detected almost immediately after delivery of a shock for accurate determination of the current status of electrical activity of the atrium. The features of low polarization and accurate sensing are important for detection and evaluation of atrial status since atrial signals have magnitudes of only about 20% to 25% those of ventricular signals because of the smaller atrial mass. The braided carbon fiber structure of electrode 21 is also desirable to provide a large effective electrical surface area (for example, in a range from three to six square centimeters) relative to its considerably smaller geometric area, which provides greater energy efficiency for defibrillation.

As with atrial electrode 21, ventricular electrode 26 of lead 27 is positioned for use as a defibrillation electrode as well as for bipolar sensing in the ventricle. For defibrillation, electrode 26 also cooperates with the metal case 15, pouch electrode 37, or pericardial electrode 36, whichever of these latter electrodes is used in the defibrillator implementation.

Again, a braided conductive structure for electrode 26 provides it with an effective surface area considerably larger than its actual exposed surface area. As an alternative, the electrode may be composed of fine metallic filaments and fibers of platinum iridium alloy, braided together to offer similarly desirable electrode characteristics.

Thus, the tip electrodes of leads 22 and 27 are used for sensing and pacing of the respective atrial and ventricular chambers as in a conventional pacemaker, with dual-chamber pacing, dual-chamber sensing, and both triggered and inhibited response. Further, the defibrillator 13 uses a transvenous electrode for ventricular defibrillation and stimulation and an atrial bipolar lead for sensing and atrial defibrillation, so that atrial defibrillation is performed with one of the same electrodes used for atrial stimulation and sensing.

Rather than terminating at distal tip electrode 32, the latter electrode may be positioned at mid-lead of the atrial transvenous lead 22 which extends and is threaded through right atrium, ventricle, pulmonary valve, and into the left pulmonary artery, with a coil counter-electrode 42 connected to a separate conductor of the lead. With this alternative embodiment, a defibrillating waveform can be applied between electrode 42 and atrial defibrillation electrode 21 upon detection of atrial fibrillation. In that configuration, electrode 42 would replace signal generator case 15, conductive pouch 37, or lead portion 36 as the selected electrode, and enables a strong vector for the electric field through right and left atrium. Rather than placement in the left pulmonary artery, electrode 42 may be positioned in the distal coronary sinus for defibrillation of the atrium in conjunction with electrode 21.

Defibrillation of the atrium and ventricle is achieved by application of defibrillation waveforms of suitable shape and energy content between appropriate electrodes, such as electrode 36 and electrode 21 for atrial fibrillation, or between electrode 42 and electrode 21 for atrial fibrillation; or between electrode 36 and electrode 26 for ventricular fibrillation, in which atrial electrode 21 can be used additionally as either anode or cathode. The case 15 can serve as the anode for delivery of the shock as well, and can provide ground reference potential for unipolar sensing and pacing, in both chambers.

IV. Intracardiac EMG→EKG Construction

In one embodiment, the present invention contemplates a method comprising generating an rEKG pattern using intracardiac EMG vectors and EMG/sEKG correlation parameters. In one embodiment, the EMG vectors are collected from patients implanted with devices including, but not limited to, pacemakers, defibrillators, cardiac rhythm management devices, or any other device that provides intracardiac signals. Although it is not necessary to understand the mechanism of an invention, it is believed that EKG reconstruction expands the use of implantable devices generally used for arrhythmia detection and treatment, to overall cardiac diagnostics. Some advantages of using EKG reconstruction diagnostics instead of traditional EKG diagnostics is that it provides real-time continuous monitoring, which can be used for multiple purposes including but not limited to: i) ischemia detection; ii) myocardial Infarction detection; iii) electrolyte abnormalities detection; iv) assessment of effect of medications; or v) improved rhythm discrimination.

Various methods have been reported that may detect intracardiac electrical potential fields or cardiac electrogram recordings. U.S. Pat. No. 4,649,924. Further, methods have been reported for: i) automated EKG analysis of heart rate (U.S. Pat. No. 5,738,104); ii) determination of ST segment deviation (U.S. Pat. Nos. 4,546,776 and 3,868,567); iii) providing real-time monitoring of heart function via external systems (U.S. Pat. No. 4,679,144); and iv) providing computer assisted monitoring (U.S. Pat. No. 5,003,983). Methods for detecting changes in the major deflection of the electrocardiogram QRS axis and axis shift with filtering of recordings from an implantable device have also been reported. U.S. Pat. Nos. 6,324,421 & 6,397,100 (all of the above patents are herein incorporated by reference). These previously reported methods, however, do not establish a method for converting arbitrary electrical fields obtained inside the body or inside the heart from an implanted device into reconstructed surface electrocardiograms (i.e., for example, an rEKG) that are interpretable for subsequent analysis.

A specific implementation of a reconstructed vectorcardiogram (VCG) from an implanted device has been described. See, U.S. Pat. No. 6,766,190. There are however, several differences between this technique and those described herein.

For example, the '190 patent describes forming a VCG from implanted device recordings, which are compared to the Frank method. In some embodiments of the present invention, a reconstructed VCG or EKG provides an accurate reconstruction of surface EKGs thereby allowing for rapid interpretation by presently trained physicians. Further, the '190 patent does not describe or provide any method for reconstructing surface EKG tracings from measured VCGs.

The '190 patent also uses an external electrical pulse to adjust gain and determine the x-axis orientation of the VCG with regard to the externally measured EKG. In some embodiments of the present invention, this is done via a correlation algorithm obtained from single simultaneous measurement of surface EKG with recordings from the implanted device.

Algorithm methods described within the '190 patent provide that three orthogonal constant current pulses are used to determine the axes of the implanted device. In some embodiments of the present invention, no external electrical field or current generation is required to determine the orientation or adjust the gain of the implanted device—this is done by simultaneous recording from the device and surface of the heart's own electrical activity.

A technique using a matrix to convert voltage signals from an implanted device into a surface EKG has also been reported. Kroll et al., U.S. Pat. No. 6,980,850. The '850 patent describes a matrix conversion from vectorcardiograph to electrocardiogram is described using a series of weighting signals (step 352). These weighting factors are then adjusted by the device to form an emulated EKG. In some embodiments of the present invention, methods of forming a reliable surface EKG emulation are described using simultaneous recording of a surface EKG and intracardiac EKG. In one embodiment, an exact solution for the transformation from implanted recording data is calculated via matrix inversion. Although it is not necessary to understand the mechanism of an invention, it is believed that this process provides an exact orientation of the vectors that reconstruct the EKG, thereby supplying a reproduction of the tracing that can be scaled simply by multiplying by a single constant. In another embodiment, a method reconstructs the surface EKG by exhaustive search of all possible orientation of the projection vector. Although it is not necessary to understand the mechanism of an invention, it is believed that numerous scaling factors are systematically used in an algorithm to find a "best fit" of the reconstructed vector and this scaling factor is then recorded for subsequent reconstructions.

The '850 patent uses a series of weighing factors Km without determination of the axis of projection of the implanted electrogram. This is unlike the presently described embodiments wherein the relative location of the recorded vector can be determined, and thus the contribution of change from various positions (sitting/standing) can be easily compared. There is no described provision for the immediate and exact calculation of the relative orientation of the recorded vector in the '850 patent.

In one embodiment, the present invention contemplates a method comprising calculating the relative spatial orientation of intracardiac EMG device leads to that of traditional sEKG electrodes (i.e., for example, a 12-way electrode pattern). Although it is not necessary to understand the mechanism of an invention, it is believed that transformation of implanted device intracardiac vector recordings to form reconstruction correlations of the surface electrocardiogram uses knowledge of the spatial orientation of the leads.

In one embodiment, the present invention contemplates a method comprising recording a simultaneous traditional sEKG with an implanted device EMG recording by calculating EMG/sEKG correlations. In one embodiment, the calculating comprises developing a transformation algorithm capable of recreating an orthogonal vectorcardiogram and/or reconstructed electrocardiogram. In one embodiment, the sEKG and intracardiac EMG recordings are made at the same time. In one embodiment, the sEKG and intracardiac EMG recordings are made at different times. Although it is not necessary to understand the mechanism of an invention, it is believed that sEKGs recorded at a different time from an intracardiac EMG recording, the patient EKG should be substantially similar during both recordings.

In one embodiment, the present invention contemplates a method comprising reconstructing an rEKG using EMG/sEKG correlations and intracardiac EMG vectors. Although it is not necessary to understand the mechanism of an invention, it is believed that once EMG/rEKG correlations are obtained in a subject, a subsequent rEKG does not require a paired sEKG for comparison. In one embodiment, the method further comprises avoiding electrical interference from near field EMGs by placing the implanted device and/or leads sufficiently far from the myocardium. In another embodiment, the method further comprises avoiding electrical interference from near field EMGs by recording from a lead during periods in cardiac cycle without adjacent myocardial depolarization.

V. Method For 12-Lead Reconstruction

In one embodiment, correlation transformations relating the intracardiac and surface/external recordings are formed according to segmental temporal indexing to the QRST depolarization pattern. In one embodiment, each portion of the cardiac depolarization cycle has its own relation between the device and surface recordings. In one embodiment, the relationship may be direct matrix transformation or include scaling, filtering, or other post-processing as needed to ensure fidelity. In one embodiment, the transformation may change based on empiric relationship as the recorded depolarization pattern changes. In one embodiment, during each segment, different or redundant device recording lead vectors may be emphasized or removed by aspects of the transformation.

In one embodiment, multiple dipoles are used as a model to generate the relationship between intracardiac and surface/external recordings. In one embodiment, these multiple dipole locations are empirically determined and located in a configuration in three-dimensional space to maximize fidelity between the correlated tracings. In one embodiment, the dipoles are assigned weighting based on their proximity to the recording lead and the temporal location of the cardiac depolarization wavefront. In one embodiment, this relationship may include temporary augmentation of the effect of a nearby dipole, or the removal of this dipole during a blanking period due to nonlinear, near-field, or other undesirable effects.

In one embodiment, complete three-dimensional models of cardiac depolarization are formed through voltage mapping from imaging or body surface potential mapping, with potential supplementation from external one-time imaging modalities including MRI or CT, and used to model the depolarization pattern and thus compute a relationship between the intracardiac device potentials and the surface EKG.

VI. Methods for Using rEKGs

In one embodiment, the present invention contemplates utilizing existing data obtained from intracardiac EMG's to generate an rEKG in real-time and continuously, for the purposes of monitoring, diagnosing, and treating patients.

Currently, there are no implantable devices being used to detect ischemia, myocardial infarction, electrolyte imbalances, or drug effects on the heart (i.e., for example, QT prolongation). Current technology has only provided implanted devices that detect EMG's for heart rhythm discrimination.

In one embodiment, the present invention contemplates a method for diagnosing and/or treating a patient for conditions selected from the group comprising ischemia, myocardial infarction, cardiac toxicity from medications, electrolyte imbalances, etc. In one embodiment, an rEKG can be used to discriminate between various forms of abnormal rhythms of both ventricular and supraventricular origins. In one embodiment, an rEKG can be used for warning the patient about an abnormality. This results in the utility of seeking early medical attention as well as initiating automated intervention by an implanted device (i.e., for example, delivery of medication or early warning to a 911-emergency frequency or other a remote medical monitoring station).

In one embodiment, the present invention contemplates a method for reconstructing an individualized 12-lead surface EKG through vector transformation from intracardiac EMG's. In one embodiment, a patient may have a 3-vector intracardiac EMG recorded. In one embodiment, a first vector is recorded from an implanted device to an RV distal tip. In one embodiment, a second vector is recorded from an implanted device to a proximal coil on an RV lead. In one embodiment, a third vector is recorded from a region selected from the group comprising the implanted device, distal coil, or proximal coil to a tip of a right atrial lead and/or left ventricular lead, or any other intrathoracic electrode system (i.e., for example, a subcutaneous array, epicardial patches or leads). In one embodiment, the method further comprises simultaneously recording a 12-lead surface EKG.

In one embodiment, the method further comprises transforming the recorded EMGs and sEKGs into a EMG/sEKG correlation parameter. Although it is not necessary to understand the mechanism of an invention, it is believed that this transformation will encompass information about lead electrodes and implanted device positions as well as about chest geometry and heart positioning within the chest. It is further believed that because the heart shifts within the chest in response to different body positions, a different transformation, and therefore a different EMG/sEKG correlation parameter, can be obtained for these multiple positions including, but not limited to, the supine, prone, standing, sitting, and decubitus positions.

In one embodiment, the method further comprises using the EMG/sEKG correlation parameter to generate an rEKG while continuously processing EMG in real time. In one embodiment, the EMG/sEKG correlation parameter is automatically changed upon receiving altered input from a positional sensor within the implanted device. In one embodiment, the altered input changes the EMG/sEKG correlation parameter from supine to prone. In one embodiment, the altered input changes the EMG/sEKG correlation parameter from standing to sitting. In one embodiment, the altered input changes the EMG/sEKG correlation parameter from sitting to decubitus.

In one embodiment, the method further comprises analyzing the rEKG in real time within the implanted device and/or a remote telemetry station. In one embodiment, the analyzing identifies an rEKG threshold exceedance. In one embodiment, the rEKG threshold exceedance identifies a condition including, but not limited to, ischemia, myocardial infarction, drug toxicity, and/or electrolyte imbalances. In one embodiment, the method further comprises alerting either the subject and/or medical personnel to take appropriate actions in response to an rEKG threshold exceedance.

VII. Calculation of an rEKG

Various mathematical techniques could be applied to reconstruct a 12-lead surface EKG from 3 independent intracardiac (IC) EMG vectors. For example, by using an IC EMG and the spatial position of the various intracardiac electrodes as determined by imaging, such as, but not limited to a CT scan or an MRI. Alternatively, by using an IC EMG and a baseline 12-lead EKG obtained simultaneously. The method described herein is only one of a multitude of possible methods. The extent of this invention disclosure is not limited to this method but encompasses all other possible methods of reconstruction of 12-lead surface EKG from IC EMGs.

A "device axes" refers to the orientation in 3-space of the basis vectors for measurement of electrical readings of the implanted device. EKG axes refer to the orientation of the vectors to which the standard cardiac electrical activity are projected (e.g. I, II, III, VI, etc.)

An arbitrary vector V on lead I may be expressed by:

$$i=V\cdot I=\Sigma(\dim)v(i)I(i) \quad (1)$$

For any vector of dimension n, v(n), a complete set of basis vectors is defined by n non-collinear vectors. Thus, for n=3 (3d space), vector v=[v(x) v(y) v(z)] on the basis vectors:

$$A=[a(x)a(y)a(z)],$$

$$B=[b(x)b(y)b(z)],$$

$$C=[c(x)c(y)c(z)],$$

where $$a=a(x)v(x)+a(y)v(y)+a(z)v(z)$$

$$b=b(x)v(x)+b(y)v(y)+b(z)v(z)$$

$$c=c(x)v(x)+c(y)v(y)+c(z)v(z)$$

and, $$[abc]=[A|B|C]\cdot[v(x)v(y)v(z)], \quad (2)$$

and $$[v(x)v(y)v(z)]=[A|B|C]^{-1}[abc]. \quad (3)$$

If one starts with an "encoded" vector v on basis i, j, and k, similarly v=[v(x) v(y) v(z)] and $$i=[i(x)i(y)i(z)]$$

$$j=[j(x)j(y)j(z)]$$

$$k=[k(x)k(y)k(z)]$$

and measured projection [i j k] on basis vectors i, j, and k, need [a b c] on basis vectors a, b, and c.

Consequently, we have:

$$v=[I|J|K]^{-1}(ijk) \quad (4)$$

and $$(abc)=[A|B|C]\cdot v \quad (5)$$

thus, $$(abc)=[A|B|C]\cdot[I|J|K]^{-1}\cdot(ijk) \quad (6)$$

This result is similar to change of basis operations as used in linear algebra.

In one embodiment, reconstruction of a known basis vector orientation of vectors A, B, and C, an arbitrary vector can be projected onto new basis using (1). In one embodiment, standard 12-lead sEKG data may be reconstructed from EKG measurement of any three non-planar vectors of known orientation through (1).

In one embodiment, the present invention contemplates the reconstruction of unknown basis vectors. Although it is not necessary to understand the mechanism of an invention, it is believed that by using multiple readings of the same electrical activity vector in three-dimensional space, it is possible to solve for an unknown basis vector set in terms of known basis vectors.

An "unknown basis set" as used herein, refers to measurements from an implanted device. A "known basis set" as used herein, refers the orientation of lead positions on a standard electrocardiogram (i.e., for example, an sEKG).

In one embodiment, the present invention contemplates solving three unknown basis vectors by using a minimum of three simultaneous measurements of known-axis projections of a given vector. In one embodiment, the solving comprises an exact solution. In one embodiment, a standard depolarization loop (a single or signal-averaged QRS complex) is simultaneously recorded in both the surface and device projection axes, thereby providing a plurality of discrete measurement points. In one embodiment, the discrete measurement points are used to calculate the EMG/sEKG correlation parameter.

Although at least one of the above embodiments provides an exact solution for three unknown basis vectors, exhaustive search approaches may also be used to find unknown implanted device axes. In one embodiment, basis vectors for the implanted device are proposed and a projection of a known ventricular cardiogram (VCG) and/or recorded sEKG tracing onto this proposed basis is calculated. The method further comprises comparing the calculated basis vector projection to recorded measurements from an implanted device, thereby providing a score based on scaled differences. The method further comprises repeating this projection and scaled score calculation for all possible basis vectors, with the best scoring vector (i.e., for example, the closest fit) is chosen as the basis vector for the implanted device.

In alternative embodiment, the exhaustive search method comprises iterative refinement, wherein the proposed basis vectors are continuously compared to the expected output and altered in a direction to improve the correlation. Although it is not necessary to understand the mechanism of an invention, it is believed that this modification provides for faster search times and ultimately increased precision.

Once the calculated EMG/sEKG correlation determines the relative axes of measurement (basis vectors) for the implanted device, the method further comprises directly calculating an rEKG using EMG input and the EMG/sEKG correlation. Alternative embodiments comprise providing an intermediate conversion of the EMG input into a vectorcardiogram and subsequent projection into known standard EKG recording leads.

VIII. Cardiac Diseases

The present invention contemplates several embodiments wherein cardiac diseases are either detected and/or treated by real-time rEKG monitoring. One advantage of the present invention is that a patient having an implanted cardiac device capable of transmitting EMG information can be continuously monitored for cardiac function.

While several illustrative cardiac diseases detected by some embodiments of the present invention are discussed below, other diseases may be detected by these embodiments as well. In one embodiment, the method detects cardiac structural diseases, including but not limited to, cardiac muscle diseases (i.e., for example, pericarditis, myocarditis, etc.). In one embodiment, the method detects pulmonary diseases (i.e., for example, pulmonary embolism, pulmonary hypertension, chronic obstructive pulmonary disease, etc.). In one embodiment, the method detects central nervous system disorders (i.e., for example, stroke, cranial bleeding, etc.). In one embodiment, the method detects cardiac conduction system diseases (i.e., for example, sick sinus syndrome, atrioventricular nodal block of degrees 1, 2 and 3, etc.). In one embodiment, the method detects respiratory rate via small variations in impedance. In one embodiment, such impedance measurements could be used to enhance the specificity of a diagnosis, and to compensate/reproduce the changes in the EKG-device relationship caused by respiratory-dependent changes in heart position.

A. Ischemic Cardiomyopathy

Ischemic cardiomyopathy is generally believed to lead to congestive heart failure due to coronary artery disease. Patients with this condition may at one time have had a heart attack, angina, or unstable angina. A few patients may not have noticed any previous symptoms. As used herein the term "ischemic" means that an organ (such as the heart) is not getting enough blood and oxygen. Ischemic cardiomyopathy results when the arteries that bring blood and oxygen to the heart are blocked. There may be a build-up of cholesterol and other substances, called plaque, in the arteries that bring oxygen to heart muscle tissue. Ischemic cardiomyopathy is the most common type of cardiomyopathy in the United States and affects approximately 1 out of 100 people, most often middle-aged to elderly men.

Risk factors for ischemic cardiomyopathy include, but are not limited to, personal or family history of heart attack, angina, unstable angina, atherosclerosis, or other coronary artery diseases; high blood pressure; smoking; diabetes; high fat diet; high cholesterol; and/or obesity.

Symptoms of ischemic cardiomyopathy include, but are not limited to, chest pain; palpitations; irregular or rapid pulse; shortness of breath; cough; fatigue, weakness, faintness; decreased alertness or concentration; decreased urine output; excessive urination at night; overall swelling; and/or breathing difficulty when lying down. A physical examination may be normal, or it may reveal signs of fluid buildup (leg swelling, enlarged liver, "crackles" in the lungs, extra heart sounds, or an elevated pressure in the neck vein). There may be other signs of heart failure. A diagnosis of ischemic cardiomyopathy is currently limited to a test showing that the pumping function of the heart is too low (i.e., for example, decreased ejection fraction). A normal ejection fraction is around 55-65%, but most ischemic cardiomyopathy patients have a much lower ejection fraction.

Several types of medications have been prescribed for ischemic cardiomyopathy including, but not limited to, angiotensin converting enzyme inhibitors (i.e., for example, captopril or lisinopril), adrenergic beta-blockers (i.e., for example, metoprolol or carvedilol), and diuretics (i.e., for example, furosemide, spironolactone, or eplerenone).

B. Angina Pectoris

Angina pectoris is referred to as a stable angina having chest pain or discomfort that typically occurs with activity or stress. The pain usually begins slowly and gets worse over the next few minutes before going away. It quickly goes away with medication or rest, but may happen again with additional activity or stress. Angina is caused by too little blood flow to the heart. The most common cause of angina is coronary heart disease (CHD). Situations that increase blood flow to the heart may cause angina in people with CHD. These include exercise, heavy meals, and stress.

Some risk factors for angina include, but are not limited to, maleness; diabetes; family history of coronary heart disease before age 50; high blood pressure; high LDL cholesterol and low HDL cholesterol; lack of exercise; obesity; and or smoking. The most predominant symptom for angina comprises chest pain that occurs behind the breastbone or slightly to the left and feels like a tightness, heavy pressure, squeezing, or crushing pain. The pain may spread to shoulder, arm, jaw, neck, back, or other areas. The pain typically occurs after activity, stress, or exertion and lasts 1 to 15 minutes and can be relieved with rest and/or nitroglycerin administration. Other medicines that may be used to treat angina include, but are not limited to, blood thinners (i.e., for example, coumadin, aspirin or clopidogrel); cholesterol-lowering drugs; and blood pressure medicines (i.e., for example, calcium channel blockers, beta blockers, and angiotensin-converting enzyme (ACE) inhibitors).

C. Myocardial Infarction

A myocardial infarction is the medical term for the more commonly used term, heart attack, and is a consequence of low blood flow causing the heart to starve for oxygen. Heart muscle dies or becomes permanently damaged. Most heart attacks are caused by a blood clot that blocks one of the coronary arteries. The coronary arteries bring blood and oxygen to the heart. If the blood flow is blocked, the heart starves for oxygen and heart cells die. A clot most often forms in a coronary artery that has become narrow because of the build-up of a substance called plaque along the artery walls. Sometimes, the plaque cracks and triggers a blood clot to form. Occasionally, sudden overwhelming stress can trigger a heart attack.

Some estimates suggest that as many as 200,000 to 300,000 people in the United States die each year before medical help is sought, thereby artificially lowering the actual diagnosis rate. It is estimated, however, that approximately 1 million patients visit the hospital each year with a heart attack. About 1 out of every 5 deaths are due to a heart attack.

Risk factors for a myocardial infarction include, but are not limited to, hereditary factors; maleness; diabetes; aging; high blood pressure; smoking; high fat diet; high LDLs and low HDL ("good") cholesterol. Alternatively, higher-than-normal levels of homocysteine, C-reactive protein, and fibrinogen may also increase myocardial infarction risk.

While chest pain is the predominant symptom of a myocardial infarction, sometimes little or no chest pain occurs (i.e., for example, a silent heart attack). The pain may be felt in only one part of the body or move from your chest to your arms, shoulder, neck, teeth, jaw, belly area, or back. The pain can be severe or mild and feel like a squeezing or heavy pressure; a tight band around the chest; heavy chest; and/or bad indigestion. The Pain usually lasts longer than 20 minutes and, unlike angina pectoris, rest and nitroglycerin does not completely relieve the pain. Other symptoms of a heart attack include but are not limited to, shortness of breath; nausea or vomiting; anxiety; cough; fainting; light-headedness; dizziness; palpitations; and/or sweating.

D. Electrolyte Abnormalities

Electrolytes are minerals in your blood and other body fluids that carry an electric charge. It is important for the balance of electrolytes in your body to be maintained, because they affect the amount of water in your body, blood pH, muscle action, and other important processes. You lose electrolytes when you sweat, and these must be replenished by drinking lots of fluids.

Electrolytes exist in the blood as acids, bases, and salts (such as sodium, calcium, potassium, chlorine, magnesium, and bicarbonate) and can be measured by laboratory studies of the blood serum.

Any increased and/or decreased level of blood serum electrolyte alter the ability of a cell membrane (i.e., for example, a cardiac cell membrane) to properly maintain its electrical potential. In the case of a cardiac cell membrane an altered electrical potential has an adverse effect on the ability to depolarize and maintain a synchronized heart beat. Such a condition can lead to heart rhythm abnormalities such are ventricular tachycardia, supraventricular tachycardia, atrial arrhythmias, and/or ventricular arrhythmias.

E. Cardiac Arrhythmias

A cardiac arrhythmia is generally considered any disorder of the heart rate or heart rhythm, such as beating too fast (i.e., for example, tachycardia), too slow (i.e., for example, bradycardia), or beating irregularly.

Normally, a 4 chambered heart (i.e., for example, 2 atria and 2 ventricles) contract in a very specific, coordinated manner. The electrical impulse that signals a heart to contract in a synchronized manner begins in the sinoatrial node (SA node), which is a group of cells that regularly, and spontaneously, depolarize thereby acting as a natural pacemaker. The depolarization signal leaves the SA node and travels through the 2 upper chambers (atria). Then the depolarization signal passes through another node (the AV node), and finally, through the lower chambers (ventricles). This path enables the chambers to contract in a coordinated fashion.

Problems can occur anywhere along this conduction system, causing various arrhythmias. Examples include, but are not limited to: i) supraventricular tachycardia: a fast heart rate that originates in the upper chambers (atria), wherein the most common are atrial fibrillation or flutter, and atrioventricular nodal reentry tachycardia; ii) ventricular tachycardia: a fast heart rate that originates in the lower chambers (ventricles); and iii) bradycardia: a slow heart rate due to problems with the SA node's pacemaker ability, or other interruption in conduction through the natural electrical pathways of the heart.

The risks of getting a tachycardia or bradycardia varies greatly, depending on the condition of your heart, prior heart attack, blood chemistry imbalances, or endocrine abnormalities.

Arrhythmias may also be caused by some substances or drugs, including, but not limited to, adrenergic beta blockers, psychotropics, sympathomimetics, caffeine, amphetamines, or cocaine. Sometimes antiarrhythmic medications—prescribed to treat one type of arrhythmia—can actually cause another type of arrhythmia. Some types of arrhythmias may be life-threatening if not promptly and properly treated.

Symptoms of arrhythmias may include, but are not limited to, fast or slow heart beat, palpitations; skipping beats; fainting; light-headedness; dizziness; chest pain; shortness of breath; changes in pulse pattern; paleness; sweating; and/or cardiac arrest Current treatment to restore a normal rhythm may include, but are not limited to, intravenous medications, electrical "shock" therapy (i.e., for example, defibrillation or cardioversion), or implanting a temporary pacemaker to interrupt the arrhythmia.

Supraventricular arrhythmias may be treated with antiarrhythmic drugs. However, some supraventricular arrhythmias can be treated and cured with radiofrequency ablation, eliminating the need for lifelong drug therapy.

Increasingly, most ventricular tachycardias are treated with an implantable cardioverter-defibrillator (ICD). As soon as arrhythmia begins, the ICD sends a shock to terminate it, or a burst of pacing activity to override it.

Bradycardias that cause symptoms can be treated by implanting a permanent pacemaker.

Experimental

I. Animal Studies

Preliminary experimental results using EKG reconstruction in pigs suggest that ischemia detection and localization occur in the major coronary artery distributions. Further, such data reflects the various effects of medications such as procainamide, isuprel, and others using the ventricular EMG vectors obtained from implanted devices (data not shown).

Animal studies have been completed using pigs showing that 12-lead EKG were reconstructed in an individualized way from intracardiac EMG's and that the resulting rEKG's can detect ischemia in the different territories of the coronary vasculature (the left anterior descending artery, the Left circumflex artery, and the right coronary artery). In these studies, an implantable defibrillator was surgically placed in pigs followed by cardiac catheterizations. During the catheterizations, the coronary arteries were temporarily occluded intracardiac signals detected by the defibrillator were recorded. 12-lead sEKG's were also recorded at baseline and during coronary occlusion. rEKG's were then calculated using the sEKG and EMG data that were similar to the recorded ones and reliably identified ischemia.

Figure 3:
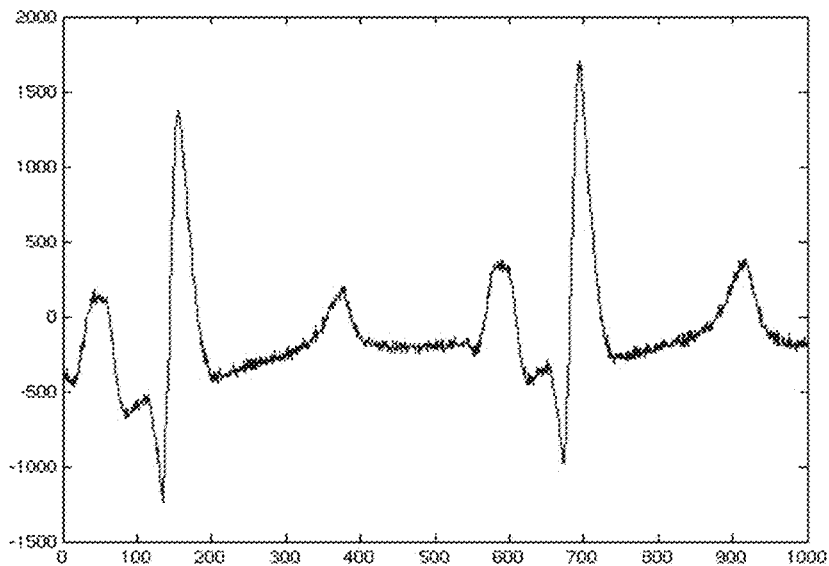
FIG. 3 presents an exemplary data comparison of a pig rEKG tracing taken from Lead I of an implanted defibrillator with its paired sEKG tracing.
Figure 3:
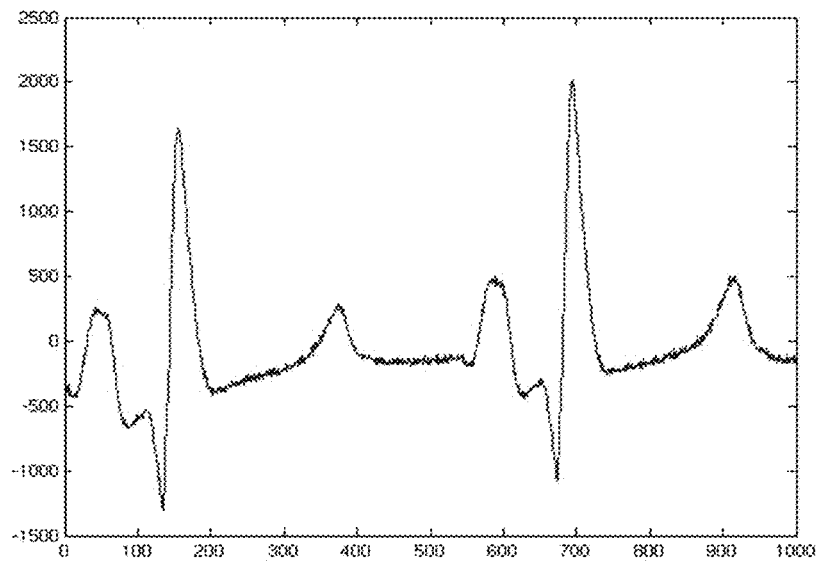
Figure 4:
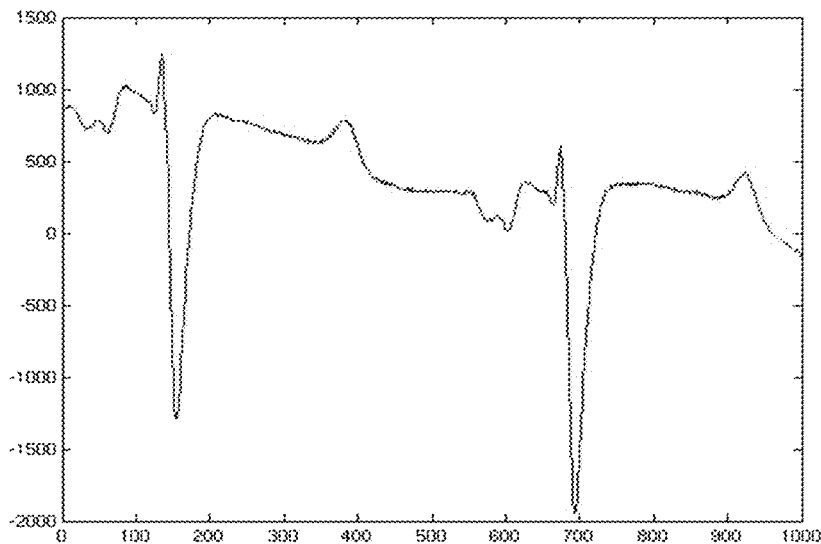
FIG. 4 presents an exemplary data comparison of a pig rEKG tracing taken from Lead III of an implanted defibrillator with its paired sEKG tracing.
Figure 4:
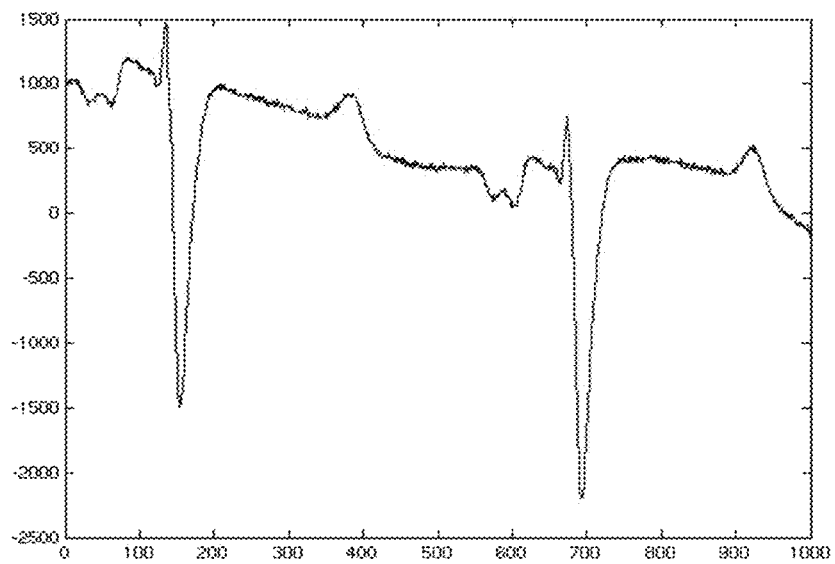
Figure 5:
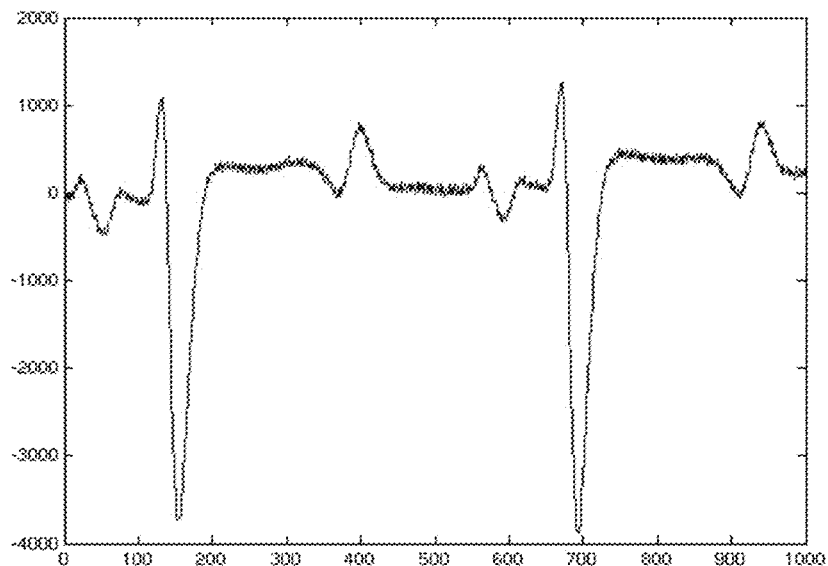
FIG. 5 presents an exemplary data comparison of a pig rEKG tracing taken from Lead V1 of an implanted defibrillator with its paired sEKG tracing.
Figure 5:
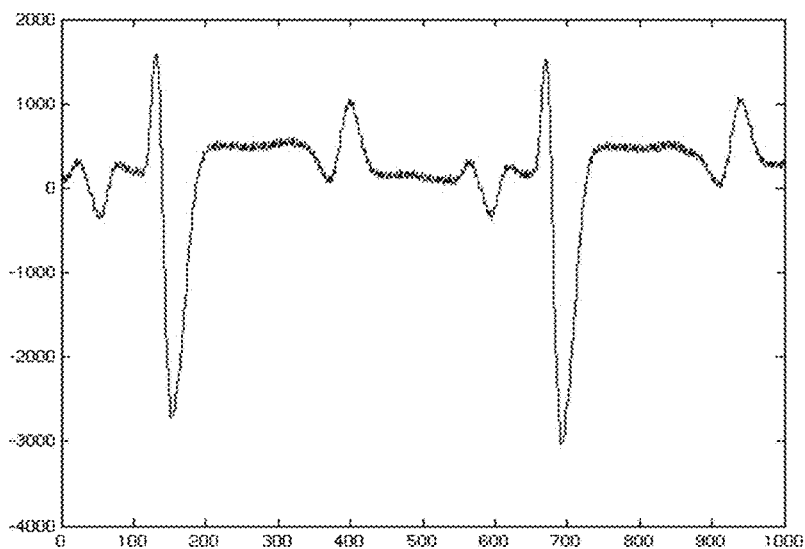

The data provides paired comparisons of rEKG tracings to the corresponding sEKG tracings for electrode leads I, III, & V1. See, FIGS. 3-5 respectively.

II. Human Patients

The method of reconstruction of a 12-lead EKG from intracardiac recordings by using multiple matrices, as opposed to only one matrix, has been examined in human patients with an implanted defibrillator. The concept of reconstructing a 12 lead EKG from the intracardiac signal recorded from the ICD involves finding a transformation that would take us from one to the other. The transformation is a matrix of numbers. The transformation can be made simple (1 matrix to convert from IC signal to surface EKG) or complex (multiple matrices). In a multiple matrix transformation, the cardiac cycle (1 beat with a P wave, a QRS wave, and a T wave) is divided into multiple portions, with each portion being represented by a separate matrix. The number of divisions can vary from one to more than two thousand. While computational complexity increases as the number of matrices increase, the result is a higher fidelity EKG reconstruction.

Figure 6A:
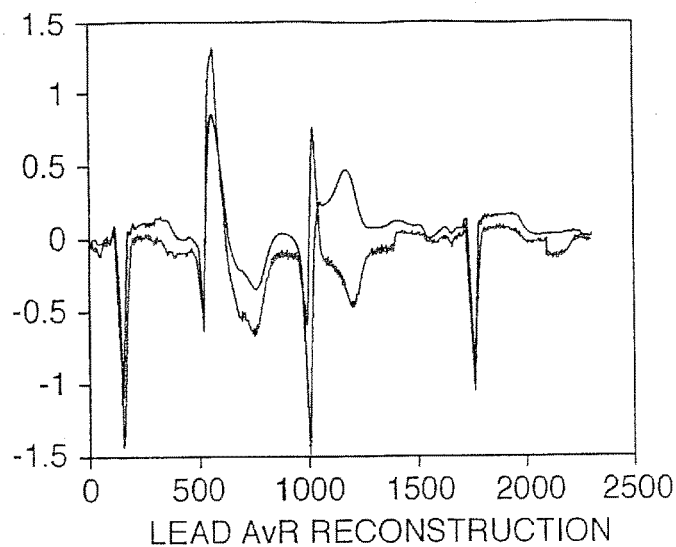
FIG. 6 depicts the superimposed tracings of recorded (blue) and reconstructed (red) EKG tracings obtained from three EKG projections (AvR, AvL and AvF) in human patients implanted with a defibrillator. Each EKG reconstruction represents 700 matrix relationships.
Figure 6B:
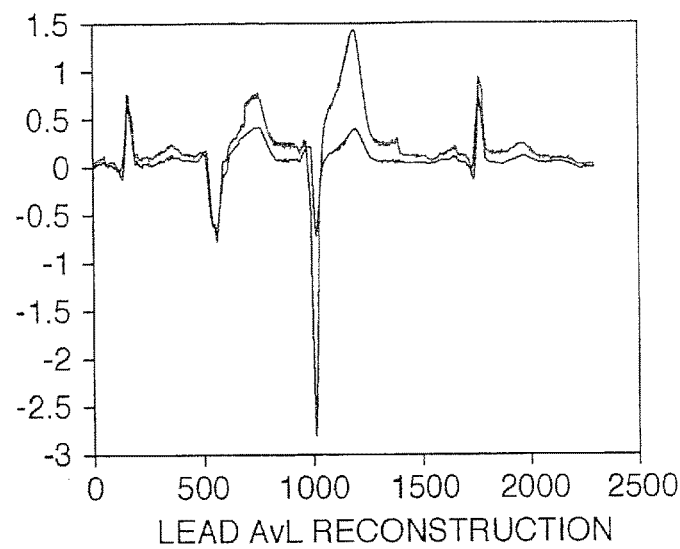
Figure 6C:
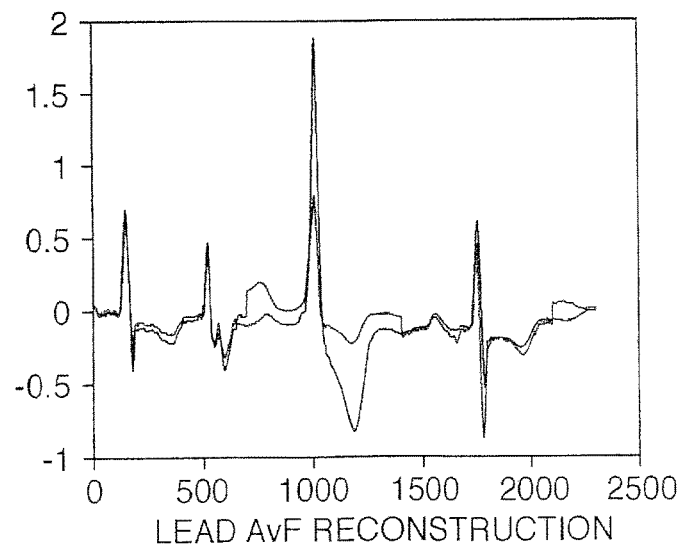
Figure 7A:
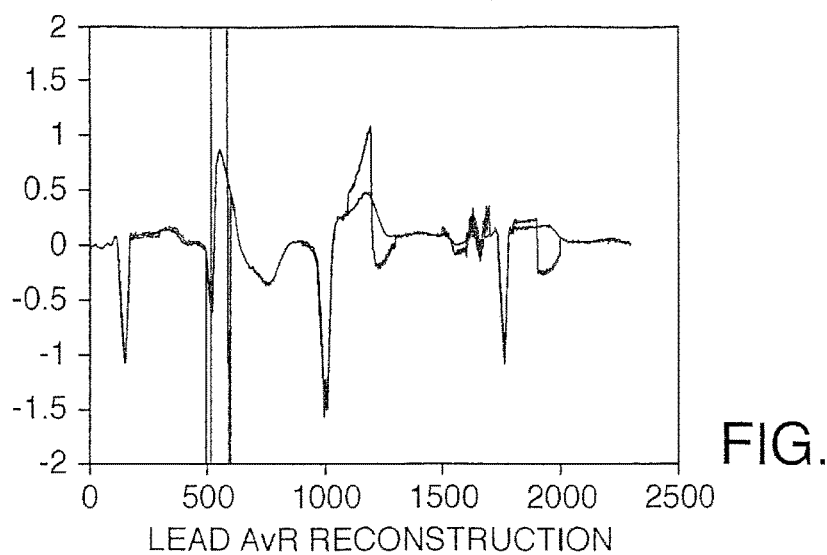
FIG. 7 depicts the superimposed tracings of recorded (blue) and reconstructed (red) EKG tracings obtained from three EKG projections (AvR, AvL and AvF) in human patients implanted with a defibrillator. Each EKG reconstruction represents 100 matrix correlations.
Figure 7B:
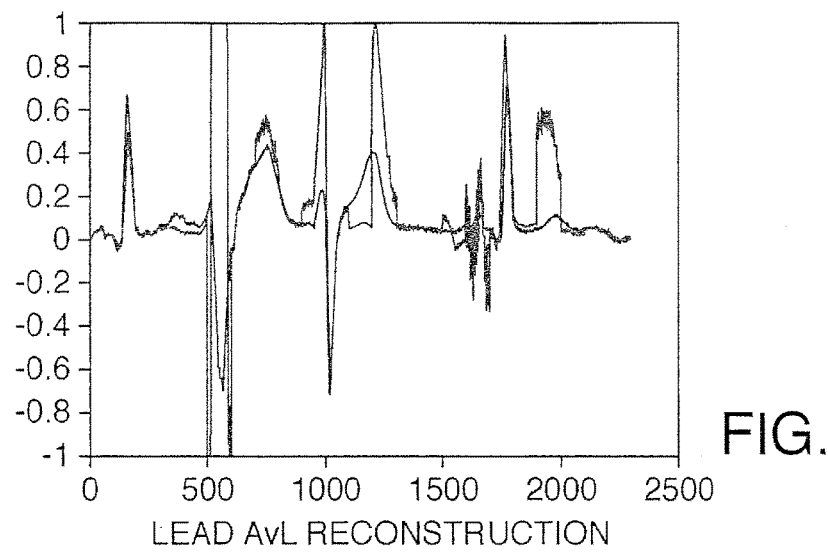
Figure 7C:
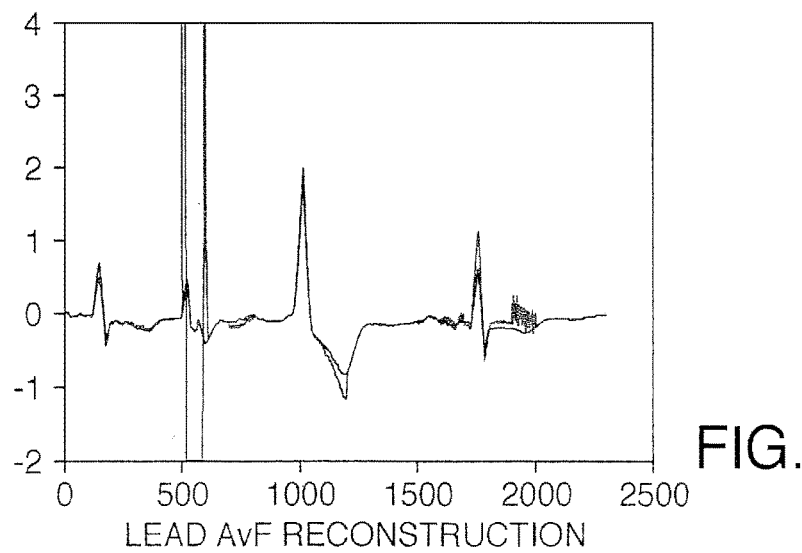

The graphs in FIGS. 6 and 7 depict the superimposed tracings of recorded (blue) and reconstructed (red) EKG tracings obtained from three EKG projections (AvR, AvL and AvF) in human patients with an implanted defibrillator. The AvR, AvL and AvF projections represent three (3) out of the standard twelve (12) projections of the 12-lead EKG.

The reconstructed EKG projections depicted in FIG. 6 represent 700 matrix relationships. Note that the major deflections are largely preserved as compared to the recorded (original) EKG tracings. FIG. 6 also demonstrates that in Lead AvR, the T wave of the third beat has an altered morphology.

The reconstructed EKG projections depicted in FIG. 7 represent 100 matrix correlations. As demonstrated by FIG. 7, areas of poor correlation have a more significant effect.

What is claimed is:

1. A method, comprising:
   a) providing:
      i) a subject exhibiting symptoms of a cardiac disease, wherein said subject has an implanted cardiac device;
      ii) a system comprising said implanted cardiac device and a microprocessor wherein said microprocessor comprises a plurality of reconstructed electrocardiogram (rEKG) threshold exceedances, wherein said microprocessor is capable of calculating a subject specific rEKG;
      iii) a testing parameter known to detect said cardiac disease;
   b) calculating said subject specific rEKG with said microprocessor while said testing parameter is administered to said subject; and
   c) comparing said subject specific rEKG to said plurality of rEKG threshold exceedances with said microprocessor by analyzing or displaying said subject-specific rEKG such that said cardiac disease is diagnosed, and
   d) signaling a warning with said implanted cardiac device about said diagnosed cardiac disease.

2. The method of claim 1, wherein said diagnosed cardiac disease comprises ischemia.

3. The method of claim 1, wherein said diagnosed cardiac disease comprises electrolyte abnormalities.

4. The method of claim 1, wherein said diagnosed cardiac disease comprises a myocardial infarction.

5. The method of claim 1, wherein said analyzing said rEKG comprises heart rhythm discrimination.

6. The method of claim 1, wherein said testing parameter comprises at least one medication.

7. The method of claim 1, wherein said testing parameter comprises a stress test.

8. The method of claim 1, wherein said testing parameter comprises a salt complex.

9. The method of claim 1, wherein said warning is in response to at least one of said plurality of threshold exceedances.

10. The method of claim 1, wherein said warning establishes said diagnosis of said cardiac disease.

11. The method of claim 1, wherein said warning is in regards to delivery of a medication.

12. The method of claim 1, wherein said warning is transmitted to a remote medical monitoring station.

13. The method of claim 1, wherein said warning is transmitted to an emergency frequency.

14. The method of claim 13, wherein said emergency frequency is a telephone 911 emergency frequency.

* * * * *